United States Patent [19]
Merkle et al.

[11] Patent Number: 5,939,584
[45] Date of Patent: Aug. 17, 1999

[54] PROCESS FOR PREPARING SOLID, FREE-FLOWING WATER-SOLUBLE SALTS OF ARYLOXY-$C_1$-$C_4$-ALKANECARBOXYLIC ACIDS

[75] Inventors: Hans Rupert Merkle; Karl Siegfried Brenner, both of Ludwigshafen; Erich Fretschner, Neckarsteinach; Michael Schönherr, Frankenthal; Anne van Gastel, Neustadt-Königsbach, all of Germany

[73] Assignee: BASF Aktiengesellschaft, Ludwigshafen, Germany

[21] Appl. No.: 08/849,715

[22] PCT Filed: Dec. 13, 1995

[86] PCT No.: PCT/EP95/04934

§ 371 Date: Jun. 18, 1997

§ 102(e) Date: Jun. 18, 1997

[87] PCT Pub. No.: WO96/20155

PCT Pub. Date: Jul. 4, 1996

[30] Foreign Application Priority Data

Dec. 23, 1994 [DE] Germany .............. 44 46 387

[51] Int. Cl.$^6$ ..................... C07C 59/48
[52] U.S. Cl. ........................ 562/471
[58] Field of Search ............... 562/471

[56] References Cited

U.S. PATENT DOCUMENTS

| | | | |
|---|---|---|---|
| 2,694,625 | 11/1954 | Warren | 71/2.6 |
| 2,792,295 | 5/1957 | Wright | 71/2.1 |
| 2,992,913 | 7/1961 | Pfeiffer | 71/2.6 |
| 3,023,096 | 2/1962 | Guth | 71/2.4 |
| 3,208,843 | 9/1965 | Guth | 71/2.6 |
| 3,284,186 | 11/1966 | Pass et al. | 71/2.6 |
| 3,674,836 | 7/1972 | Creger | 562/471 |
| 4,270,948 | 6/1981 | Takahashi et al. | 71/100 |
| 4,766,220 | 8/1988 | Gras | 546/302 |
| 5,266,553 | 11/1993 | Champion et al. | 504/206 |

FOREIGN PATENT DOCUMENTS

| | | |
|---|---|---|
| 9 285 | 4/1980 | European Pat. Off. . |
| 883 606 | 7/1953 | Germany . |
| 2520262 | 5/1975 | Germany . |
| 2531643 | 7/1975 | Germany . |
| 30 24 265 | 6/1980 | Germany . |
| 5058944 | 3/1993 | Japan . |

Primary Examiner—Paul J. Killos
Attorney, Agent, or Firm—Keil & Weinkauf

[57] ABSTRACT

Process for preparing solid, free-flowing water-soluble salts of aryloxy-$C_1$–$C_4$-alkanecarboxylic acids by reacting the aryloxy-$C_1$–$C_4$-alkanecarboxylic acids with a salt-forming base, the salt formation taking place in the melt in the presence or absence of an entraining agent suitable for the azeotropic removal of water or in solution in the presence of an entraining agent suitable for the azeotropic removal of water and, if appropriate, removing the entraining agent from the reaction mixture during the reaction or subsequently and then isolating the solid salts in a customary manner.

6 Claims, No Drawings

PROCESS FOR PREPARING SOLID, FREE-FLOWING WATER-SOLUBLE SALTS OF ARYLOXY-$C_1$-$C_4$-ALKANECARBOXYLIC ACIDS

The present invention relates to a process for preparing solid, free-flowing water-soluble salts of aryloxy-$C_1$-$C_4$-alkanecarboxylic acids.

The aryloxyalkanecarboxylic acids, in particular the aryloxyacetic acids, 2-aryloxypropanoic acids and 4-aryloxybutanoic acids, substance class, in which an aryl radical is in particular to be understood as meaning a phenyl radical substituted by halogen, such as bromine or chlorine, and/or $C_1$-$C_4$-alkyl, in particular methyl, has been known for a long time for its herbicidal action. A compilation is found eg. in K. H. Büchel: Pflanzenschutz und Schädlingsbekämpfung (Crop Protection and Pest Control), Georg Thieme Verlag, Stuttgart 1977, pp. 173–175. The following active compounds eg.: 2,4-dichlorophenyoxyacetic acid (2,4-D), 2-methyl-4-chlorophenoxyacetic acid (MCPA), 2-(2-methyl-4-chlorophenoxy)-propionic acid (mecoprop, MCPP), 2-(2,4-dichlorophenoxy)propionic acid (dichlorprop, 2,4-DP), 2-(2,4,5-trichlorophenoxy)propionic acid (fenoprop), 4-(2,4-dichlorophenoxy)butanoic acid (2,4-DB) and 4-(2-methyl-4-chlorophenoxy)butanoic acid (MCPB) and their salts, in particular those of sodium, potassium, ethylammonium and dimethylammonium, found commercial use (cf. also The Pesticide Manual, 9th ed., published by the British Crop Protection Council, 1991).

The marketing of the aryloxycarboxylic acids, also called phenoxycarboxylic acids in the following, mainly took place in the form of their salts as liquid concentrates. Aqueous solutions of phenoxycarboxylic acid salts are disclosed eg. in U.S. Pat. No. 2,694,625, U.S. Pat. No. 2,992,913 and U.S. Pat. No. 3,284,186. These salt solutions are handled in plastic or metal containers whose disposal or cleaning caused public discussions.

There was therefore a need to make these compounds available in solid and, at the same time, readily water-soluble form.

Even in 1950, granulated formulations of halogenated phenoxyacetic acids were published in which, to avoid dust contents, auxiliaries such as clay, chalk, gypsum or artificial fertilizer were added (U.S. Pat. No. 2,792,295).

Solid, free-flowing, water-soluble lithium salts of phenoxycarboxylic acids were also described (U.S. Pat. No. 3,208,843). U.S. Pat. No. 3,023,096 describes the preparation of the potassium and lithium salts of dichlorophenoxyacetic acid.

In U.S. Pat. No. 5,266,553, the prior art is discussed in detail, and for the preparation of solid salts it is proposed to neutralize the corresponding aryloxycarboxylic acids with a base and to convert the resulting aqueous solution or mash into the solid salts by evaporating water under controlled conditions. The solid salts can also be prepared by evaporating water from the corresponding commercially available aryloxy salt solutions.

Publications on the preparation of solid, free-flowing salts of optically active phenoxypropionic acids were hitherto unknown.

The optically active phenoxypropionic acids are liberated by acidifying the neutral reaction solutions obtained from the synthesis with acids, isolating and converting them into the salts (DE-A 30 24 265).

According to EP-A 0 009 285, an oily phase is separated at pH 4 from the neutral reaction solution partly prepared with hydrochloric acid, which is extracted with ether. After evaporating the ether, the corresponding optically acid phenoxypropionic acids are obtained.

It is an object of the present invention to make available a process for preparing solid, free-flowing and readily water-soluble salts of aryloxycarboxylic acids, which is also suitable, in particular, for preparing optically active propionates, of which, as is known, the D-(+)-enantiomers are exclusively biologically active (cf. K. H. Büchel, loc. cit. and Kgl. Lantbruks-Högskolans, Anm. 20 (1953) 241–295).

We have found that this object is achieved by a process for preparing solid, free-flowing, water-soluble salts of aryloxy-$C_1$-$C_4$-alkanecarboxylic acids, which comprises reacting the aryloxy-$C_1$-$C_4$-alkanecarboxylic acids with a salt-forming base, the salt formation taking place in the melt in the presence or absence of an entraining agent suitable for the azeotropic removal of water or in solution in the presence of an entraining agent suitable for the azeotropic removal of water and, if appropriate, removing the entraining agent from the reaction mixture during the reaction or subsequently and then isolating the solid salts in a customary manner.

Entraining agents suitable for the reaction are, for example, cyclohexane, toluene, petroleum ether and advantageously low molecular weight alcohols such as, in particular, $C_1$-$C_7$-alkanols and -alkanediols; especially primary, secondary and tertiary alcohols; such as eg. methanol, ethanol, propanol, isopropanol, n-butanol, i-butanol, t-butanol, pentanols, hexanols, heptanols and mixtures thereof. Particularly preferably, on account of their good separability from the reaction mixture, they only mix with water (water of reaction or eg. water added by means of the base) to a limited extent and are therefore particularly suitable for removing water from the reaction mixture. Methanol and isobutanol have proven particularly advantageous.

The conversion of the acid into its salt is carried out using the bases customary for this. Alkali metal and alkaline earth metal hydroxides, eg. sodium hydroxide, potassium hydroxide and magnesium hydroxide, alkali metal and alkaline earth metal oxides, alkali metal and alkaline earth metal carbonates or hydrogen carbonates, alkali metal or alkaline earth metal acetates and formates, ammonia and alkyl-substituted primary, secondary and tertiary amines having 1 to 4 C atoms or mixtures of these bases can be mentioned. The bases can be employed stoichiometrically or in an excess or a slightly substoichiometric amount.

Salt formation can be carried out in the melt or in solution. In the last-mentioned case the low molecular weight alcohol is advantageously used as the solvent. However, it is also possible, in addition to the alcohol, to have present water or another organic solvent such as eg. toluene, xylene and other solvents which function as water-entraining agents and are inert under the reaction conditions. Preferably, the aryloxyalkanecarboxylic acid is dissolved in the alcohol or in a mixture of alcohol plus organic solvent or in the organic solvent and then the base is added, expediently dissolved in alcohol, or, in the case of ammonia, directly as a gas.

The solvent functioning as an entraining agent, such as methanol or isobutanol, is advantageously employed in at least an amount such that the base is dissolved or well suspended.

According to a preferred embodiment of the process, salt formation is carried out in the melt. In this embodiment, the base is advantageously dissolved in the low molecular weight alcohol and added to a melt of the phenoxycarboxylic acid. The heat content of the melt can be utilized directly in order to evaporate the alcohol introduced with the base during the reaction. For example, the aryloxy-$C_1$–$C_4$-alkanecarboxylic acid can thus be treated in the melt with an alcoholic solution of the base, eg. sodium, potassium or magnesium hydroxide, and the alcohol simultaneously removed from the reaction mixture.

Of course, it is also possible to evaporate the alcohol and, if appropriate, additionally organic solvent only after reaction has taken place. During the evaporation of the solvents, water of reaction and water of crystallization can also be removed very readily from the starting substances. Reaction and drying can be carried out under normal pressure, reduced pressure or elevated pressure at from 0 to 250° C., particularly 80 to 150° C. The salts prepared according to the invention can be dried by conventional drying processes, for example by contact drying processes or convective drying processes. Shaping processes such as spray drying or spray granulation are particularly preferred.

If the reaction is carried out in the melt it is also possible to dispense with the addition of alcohol or solvent. In this case, the melts of the acids can be reacted directly with the base by intimate mixing.

According to another embodiment of the process, a solution of aryloxy-$C_1$–$C_4$-alkanecarboxylic acid salts is prepared in a low molecular weight alcohol and the solid salts are isolated from this solution by spray drying or by the spray granulation process. In this case, solutions are expediently to be preferred which are formed directly during salt formation. A solution is particularly preferred which, after reaction of the relevant phenoxy acid with the base, is present in the solvent; water of reaction or crystallization present does not interfere in this case. The solution can be sprayed at from 0 to 250° C. Temperatures from 80 to 200° C. are preferred. A spray temperature of from 120 to 160° C. is particularly favorable.

The atomization of the solution of the salts can be carried out using known atomization apparatus, such as eg. single-substance nozzles, two-substance nozzles, rotary atomizers, ultrasonic atomizers etc. (Arthur H. Lefevre, Atomization and Sprays, Hemisphere Publishing Corporation, 1989). Single-substance nozzles are preferably used, as at normal pressure a flash evaporation takes place at temperatures of the solution above the boiling temperature. Pressures in the range from 5 to 100 bar, preferably 10 to 20 bar, are used here.

The atomization of the solution can be carried out in a dryer at normal, reduced or elevated pressure. The energy for evaporating the solvent is obtained from the energy content of the solution and/or from a drying gas. The drying gas can be air, an inert gas such as nitrogen or the superheated vapor of the solvent. The drying gas can be conducted directly or recycled. For economic reasons, the recycled gas procedure is to be preferred. The temperature of the drying gas is above room temperature, preferably in the range from 100 to 450° C. Temperatures in the range from 150 to 250° C. are very particularly preferred. For economic reasons, the majority of the energy is to be supplied by the temperature of the solution. As a result, the amount of inert gas is minimized.

During the drying of the salt solutions solid particles are formed. The structure and the size of the particles are determined by the type and geometry of the dryer and the operating conditions. Spray dryers (K. Masters, Spray Drying Handbook, Logman Scientific & Technical 1991) and spray granulation dryers, for example, are suitable for drying the solution. While a powdered product is as a rule obtained in spray towers, coarser products and granules can be prepared in spray granulation dryers. On account of its tendency to agglomerate, the solution of the salts is suitable for spray granulation. Agglomeration fluidized beds and spray dryers having an integrated agglomeration fluidized bed are preferred.

The solid, free-flowing salts of phenoxycarboxylic acids prepared in the ways mentioned can be packed and stored in volume-saving paper or plastic bags. Before application, they can be dissolved very readily to give aqueous spray mixtures of defined concentrations. The disposal of these packs is simple and possible problems with plastic or metal containers contaminated by product are eliminated.

According to a further embodiment according to the invention of the process, not only individual aryloxycarboxylic acid salts, but also mixtures of salts of various aryloxycarboxylic acids can be prepared. For example, the following mixtures of two or three phenoxycarboxylic acids may be mentioned: (in each case common name, cf. The Pesticide Manual, 9th edition, 1991)

dichlorprop-P and 2,4-D;
dichlorprop-P and MCPA;
mecoprop-P and 2,4-D;
mecoprop-P and MCPA;
MCPA and 2,4-D;
mecoprop-P, dichlorprop-P and MCPA.

Instead of the optically active phenoxycarboxylic acids, their racemates can also be present in the mixture. It is furthermore possible, in addition to the phenoxycarboxylic acids, to have other herbicides selected from the group consisting of bentazone, glyphosate, glufosinate, ioxynil, bromoxynil and dicamba (cf. The Pesticide Manual, loc. cit., No. 770, 6950, 6930, 7300, 1410 and 4100) present as starting substances and to prepare the corresponding, solid salt mixtures, in particular of sodium, potassium or ammonium salts, directly from the mixture thereof. The following mixtures may be mentioned as examples:

bentazone and 2,4-D;
bentazone and dichlorprop-P;
bentazone and mecoprop-P;
bentazone and MCPA;
bentazone and MCPB;
bentazone and MCPB and MCPA;
bentazone and 2,4-DB;
bentazone and MCPA.

The sodium or potassium salts are preferably formed from these mixtures by the process according to the invention. Instead of bentazone in the abovementioned mixtures, glyphosate, glufosinate, ioxynil, bromoxynil and dicamba can be reacted in a similar manner.

The following examples illustrate the invention.

Preparation Examples

EXAMPLE 1

Sodium 2-methyl-4-chlorophenoxyacetate 20 parts (0.1 mol) of 2-methyl-4-chlorophenoxyacetic acid (MCPA) (94.7%) are melted at 130° C. and reacted with 45 parts (0.1 mol, based on 100%) of 8.9% strength sodium hydroxide solution with simultaneous removal of methanol by distillation. After complete removal of methanol by distillation, 23.5 parts of MCPA-sodium of m.p. 227–230° C. are obtained, containing 80.8% MCPA, which corresponds to a yield of 99.7%.

EXAMPLE 2

MCPA-potassium

A melt of 20 parts (0.1 mol) of MCPA (94.7%) is reacted with 100 ml of 1 molar methanolic potassium hydroxide solution (0.1 mol) at 130° C. with removal of methanol by distillation. After complete removal of methanol by distillation, 25.1 parts of MCPA-potassium are obtained, containing 73.3% of MCPA of m.p. 200–205° C., which corresponds to a yield of 100%.

EXAMPLE 3

Potassium D-2-methyl-4-chlorophenoxypropionate (D-CMPP-potassium)

A melt of 21.5 parts of D-CMPP (0.1 mol) with a CMPP content of 97.7% which is divided into the D/L isomers 97.1:2.9, is reacted with 47.5 parts (0.1 mol) of isobutanolic potassium hydroxide (11.8% strength) at 130° C. with simultaneous removal of isobutanol by distillation. After evaporating the isobutanol, 25 parts of D-CMPP-potassium having an acid content of 83.3%, consisting of 97.5% D and 2.5% L enantiomer, of m.p. 240–245° C. are obtained, which corresponds to a yield of 99.5%.

EXAMPLE 4

Sodium D-2,4-dichlorophenoxypropionate (D-2,4-DP-sodium)

A melt of 23.5 parts of D-2,4-DP (0.1 mol) with an acid content of 97.1%, consisting of 93.9% D- and 6.1% L-isomers, is reacted at 130° C. with 45 parts (0.1 mol) of a methanolic sodium hydroxide solution 18.9% strength, methanol being evaporated. After evaporation to dryness, 25.9 parts of D-2,4-DP-sodium of m.p. 75–80° C. having a D+L content of 83.3% (D: 93.6%, L: 6.4%) are obtained, which corresponds to a yield of 100%.

EXAMPLE 5

Potassium D-2,4-dichlorophenoxypropionate-(D-2,4-DP-potassium)

200ml (0.1 mol, based on KOH calc. 100%) of 0.5 molar ethanolic potassium hydroxide solution are added at 130° C. with removal of methanol by distillation to a melt of 23.5 parts of D-2,4-DP (0.1 mol) (D+L content 97.1%; D: 93.9%, L 6.1%). After completely evaporating the solvent, 27 parts of D-2,4-DP-potassium (D+L 84%; D: 94.1, L: 5.9%) of m.p. 195° C., are obtained, which corresponds to a yield of 100%.

EXAMPLE 6

A solution of 100 g of potassium salt of D-2,4-DP, 6.5 g of water (water of crystallization and reaction) and 90 g (1.22 mol) of isobutanol was converted to a powder by spray drying in a laboratory spray tower. The solution was at room temperature and was atomized in drying air at 120° C. A Schlich model 970 type two-substance nozzle was used for the atomization. The atomization gas was heated to 180° C.

EXAMPLE 7

Ammonium D-2,4-dichlorophenoxypropionate (D-2,4-DP-ammonium)

47 parts of D-2,4-DP (0.2 mol) with an acid content of 97.1%, consisting of 93.9% D- and 6.1% L-isomers, are dissolved in 200 parts of methanol and treated with 3.6 (0.21 mol) parts of ammonia. After completely evaporating methanol, 52.6 parts of D-2,4-DP-ammonium of m.p. 109° C. having a D+L content of 86.7% (D: 94.1%, L: 5.9%) are obtained, which corresponds to a yield of 100%.

EXAMPLE 8

Dimethylammonium D-2,4-dichlorphenoxypropionate (D-2,4-DP-dimethylammonium)

23.5 parts of D-2,4-DP (0.1 mol) with an acid content of 97.1%, consisting of 93.9% D- and 6.1% L-isomers, are reacted with 36 parts (0.1 mol) of 12.5% strength methanolic dimethylamine solution. After completely evaporating methanol, 27.6 parts of D-2,4-DP-dimethylammonium of m.p. 83° C. having a D+L content of 82.5% (D: 93.7%, L: 6.3%) are obtained, which corresponds to a yield of 100%.

EXAMPLE 9

Potassium D-2-methyl-4-chlorophenoxypropionate (D-CMPP-potassium)

A melt of 10.75 parts of D-CMPP (0.05 mol) with a CMPP content of 98.1%, which is divided into the D/L isomers 97.6:2.4 is reacted at 130° C. and with simultaneous removal of methanol and water by distillation with 27.5 ml (0.05 mol) of 2 molar methanolic potassium hydroxide solution which contains 10% water. After evaporating the methanol and water, 13.4 parts of D-CMPP-potassium are obtained. The content of D-CMPP is 82.4% (D: 96.7%, L: 3.3%), which corresponds to a yield of 100%. M.p.: 227° C.

EXAMPLE 10

Potassium D-2-methyl-4-chlorophenoxypropionate (D-CMPP-potassium)

A melt of 10.5 parts of D-CMPP (0.05 mol) with a CMPP content of 98.1% which is divided into the D/L isomer 97.6:2.4 is reacted with 32 parts (0.05 mol) of isobutanolic potassium hydroxide solution (9.2% strength) which contains 10% water at 130° C. with simultaneous removal of isobutanol and water by distillation. After evaporating isobutanol and water, 12.8 parts of D-CMPP-potassium are obtained. The content of D-CMPP is 79.2% (D: 96.4%, L: 3.6%), which corresponds to a yield of 96.1% of theory. M.p.: 205° C.

EXAMPLE 11

Potassium D-2-methyl-4-chlorophenoxypropionate (D-CMPP-potassium)

A solution of 10.5 parts of D-CMPP (0.05 mol) with a CMPP content of 98.1% which is divided into the D/L isomers 97.6:2.4 and 10 ml of toluene is reacted with 25 ml (0.05 mol) of 2 molar methanolic potassium hydroxide solution under reflux with simultaneous removal of toluene and methanol by distillation. After evaporating methanol and toluene, 12.7 parts of D-CMPP-potassium are obtained. The content of D-CMPP is 80.6% (D: 96.4%, L: 3.6%), which corresponds to a yield of 97% of theory. M.p.: 224° C.

EXAMPLE 12

Potassium D-2-methyl-4-chlorophenoxypropionate (D-CMPP-potassium)

A solution of 10.5 parts of D-CMPP (0.05 mol) with a CMPP content of 98.1% which is divided into the D/L isomers 97.6:2.4 and 10 ml of isobutanol is reacted with 14 parts (0.05 mol) of aqueous potassium hydroxide solution (20% strength) under reflux with simultaneous removal of isobutanol and water by distillation. After evaporating isobutanol and water, 14.4 parts of D-CMPP-potassium are obtained. The content of D-CMPP is 72% (D: 96.4% L: 3.6%), which corresponds to a yield of 98.3% of theory. M.p.: 198° C.

EXAMPLE 13

Potassium D-2,4-dichlorophenoxypropionate with bentazone-potassium

A solution of 16.9 parts (0.07 mol) of bentazone (99.5%) and 42.7 parts (0.07 mol) of isobutanolic potassium hydroxide solution (9.2% strength) is reacted with a solution of 11.75 parts (0.05 mol) of D-2,4-DP (D+L content 97.1%; D: 93.9%, L: 6.1%) in 30.5 parts (0.05 mol) of isobutanolic potassium hydroxide solution (9.2% strength) with simultaneous removal of isobutanol by distillation. After evaporating to dryness, 37.6 parts of a D-2,4-DP-potassium and bentazone-potassium mixture in the ratio 1:1.4 are obtained. The content of D-2,4-DP is 30.8% (D: 94.0%, L: 6.0%), which corresponds to a yield of 100%. M.p.: 75° C.

EXAMPLE 14

Ammonium D-2,4-dichlorophenoxypropionate with bentazone-ammonium

A solution of 16.9 parts (0.07 mol) of bentazone (99.5%) and 12.7 parts (0.07 mol) of methanolic ammonia solution (9.4% strength) is reacted with a solution of 11.75 parts (0.05 mol) of D-2,4-DP (D+L content 97.1%; D: 93.9%, L: 6.1%) in 9 parts (0.05 mol) of methanolic ammonia solution (9.4% strength) with simultaneous removal of methanol by distillation. After evaporating to dryness, 30.3 parts of a D-2,4-DP-ammonium and bentazone-ammonium mixture in the ratio 1:1.4 are obtained. The content of D-2,4-DP is 36.9% (D: 94%, L: 6.0%), which corresponds to a yield of 98% of theory. M.p.: 205° C.

EXAMPLE 15

Potassium D-2-methyl-4-chlorophenoxypropionate with bentazone-potassium

A solution of 16.9 parts (0.07 mol) of bentazone (99.5%) and 42.7 parts (0.07 mol) of isobutanolic potassium hydroxide solution (9.2% strength) is reacted with a solution of 16.1 parts (0.075 mol) of D-CMPP (D+L content 98.1%; D: 97.6%, L: 2.4%) in 45.7 parts (0.075 mol) of isobutanolic potassium hydroxide solution (9.2% strength) with simultaneous removal of isobutanol by distillation. After evaporating to dryness, 38.8 parts of a D-CMPP-potassium and bentazone-potassium mixture in the ratio 1.5:1.4 are obtained. The content of D-CMPP is 39.6% (D: 97.6%, L: 2.4%), which corresponds to a yield of 97.3% of theory. M.p.: 209° C.

EXAMPLE 16

Potassium 2-methyl-4-chlorophenoxyacetate with bentazone-potassium

A solution of 12.1 parts (0.05 mol) of bentazone (99.5%) and 30.5 parts (0.05 mol) of isobutanolic potassium hydroxide solution (9.2% strength) is reacted with a solution of 6 parts (0.03 mol) of MCPA (94.7%) in 18.3 parts (0.03 mol) of isobutanolic potassium hydroxide solution (9.2% strength) with simultaneous removal of isobutanol by distillation. After evaporating to dryness, 18.1 parts of an MCPA-potassium and bentazone-potassium mixture in the ratio 0.6:1 are obtained. The content of MCPA is 33.2%, which corresponds to a yield of 100%. M.p.: 233° C.

EXAMPLE 17

Potassium 2-methyl-4-chlorophenoxyacetate 6.6 parts (0.1 mol) of powdered potassium hydroxide (85%) are introduced into a melt of 20 parts (0.1 mol) of MCPA (93.3%) with stirring and the mixture is kept at 130° C. for 30 minutes. After solidification, 26 parts of MCPA-potassium having an MCPA content of 71.8% are obtained, which corresponds to a yield of 100%. M.p.: 203° C.

EXAMPLE 18

Sodium 2,4-dichlorophenoxyacetate with bentazone-sodium 24.6 parts of an aqueous bentazone-sodium solution (content=48.8%) are reacted with a solution of 12.2 parts (0.05 mol) of 2,4-dichlorophenoxyacetic acid in 200 parts (0.05 mol) of 1% strength sodium hydroxide solution and 50 parts of isobutanol. Isobutanol/$H_2O$ is then evaporated. After evaporating to dryness, 25.3 parts of a sodium 2,4-dichlorophenoxyacetate and bentazone-sodium mixture are obtained. The content of 2,4-dichlorophenoxyacetic acid is 41.8%, which corresponds to a yield of 100%. M.p.: 130° C.

EXAMPLE 19

Potassium D-2-methyl-4-chlorophenoxypropionate with bromoxynil-potassium

A solution of 10.75 parts (0.05 mol) of D-CMPP (D+L content 98.1%; D: 97.6%, L: 2.4%) in 30.1 parts (0.05 mol) of isobutanolic potassium hydroxide solution (9.3% strength) is reacted with a suspension of 13.9 parts (0.05 mol) of bromoxynil in 30.1 parts (0.05 mol) of isobutanolic potassium hydroxide solution with simultaneous removal of isobutanol by distillation. After evaporating to dryness, 28.4 parts of a D-CMPP-potassium and bromoxynil-potassium mixture are obtained. The content of D-CMPP is 36.2% (D: 97.6%, L: 2.4%), which corresponds to a yield of 97.4%. M.p.: 215° C.

EXAMPLE 20

Potassium D-2-methyl-4-chlorophenoxypropionate with ioxynil-potassium

A solution of 5.4 parts (0.025 mol) of D-CMPP (D+L content 98.1%; D: 97.6%, L: 2.4%) in 15.05 parts (0.025 mol) of isobutanolic potassium hydroxide solution (9.3% strength) is reacted with a suspension of 9.3 parts (0.025 mol) of ioxynil in 15.05 parts (0.025 mol) of isobutanolic potassium hydroxide solution (9.3% strength) with simultaneous removal of isobutanol by distillation. After evaporating to dryness, 16.7 parts of a D-CMPP-potassium and ioxynil-potassium mixture are obtained. The content of D-CMPP is 30.5% (D: 97.6%, L: 2.4%), which corresponds to a yield of 96.6%. M.p.: 205° C.

EXAMPLE 21

Sodium 2-methyl-4-chlorophenoxyacetate with bromoxynil-sodium

A solution of 10 parts (0.05 mol) of MCPA in 22.5 parts of methanolic sodium hydroxide solution (8.9% strength) is reacted with a suspension of 13.85 parts (0.05 mol) of bromoxynil in 22.5 parts (0.05 mol) of methanolic sodium hydroxide solution (8.9% strength) with simultaneous removal of methanol by distillation. After evaporating to dryness, 27.4 parts of a MCPA-sodium and bromoxynil-sodium mixture are obtained. The content of MCPA is 35.0%, which corresponds to a yield of 100%. M.p.: >300° C.

EXAMPLE 22

Sodium D-2-methyl-4-chlorophenoxypropionate with ioxynil-sodium

A solution of 5.4 parts (0.025 mol) of D-CMPP (D+L content 98.1%; D: 97.6%, L: 2.4%) in 11.25 parts (0.025 mol) of methanolic sodium hydroxide solution (8.9% strength) is reacted with a suspension of 9.3 parts (0.025 mol) of ioxynil in 11.25 parts (0.025 mol) of methanolic sodium hydroxide solution (8.9% strength) with simultaneous removal of methanol by distillation. After evaporating to dryness, 16.7 parts of a D-CMPP-sodium and ioxynil-sodium mixture are obtained. The content of D-CMPP is 32.4% (D: 97.6%, L: 2.4%), which corresponds to a yield of 95.2%. M.p.: 288° C.

EXAMPLE 23

Magnesium D-2-methyl-4-chlorophenoxypropionate

A suspension of 2.9 parts (0.05 mol) of magnesium hydroxide in 2.9 parts of water is added to a solution of 21.5 parts (0.1 mol) of D-CMPP (D+L content 97.7%; D: 95.7%, L: 4.3%) in 21.5 parts of isobutanol with simultaneous removal of isobutanol and water by distillation. After evaporating to dryness, 22.8 parts of D-CMPP-magnesium having an acid content of 91.7% are obtained, consisting of 95.7% D and 4.3% L enantiomer—of m.p. >300° C., which corresponds to a yield of 99.6%.

EXAMPLE 24

Potassium D-2-methyl-4-chlorophenoxypropionate 34.5 parts (0.05 mol) of 20% strength potassium carbonate solution are added dropwise to a melt of 21.5 parts (0.1 mol) of D-CMPP (D+L content 97.7%; D: 95.7%, L: 4.3%) at 130° C., $CO_2$ being released which drives off part of the water. After completely evaporating the water, 25.6 parts of D-CMPP-potassium having an acid content of 82.2% are obtained, consisting of 95.5% D and 4.5% L enantiomer—of m.p. 236°–238° C., which corresponds to a yield of 100%.

EXAMPLE 25

Magnesium D-2-methyl-4-chlorophenoxypropionate

A suspension of 2 parts (0.05 mol) of magnesium oxide in 18 parts of water is added to a solution of 21.4 parts (0.1 mol) of D-CMPP (D+L content 98.3%; D: 97.4%, L: 2.6%) in 25 parts of isobutanol with simultaneous removal of isobutanol and water by distillation. After evaporating to dryness, 22.9 parts of D-CMPP-magnesium having an acid content of 89.1% are obtained, consisting of 97.4% D and 2.6% L enantiomer of m.p. >300° C., which corresponds to a yield of 97.4%.

EXAMPLE 26

Magnesium D-2-methyl-4-chlorophenoxypropionate

A suspension of 86 parts (0.4 mol) of D-CMPP (D+L content 97.7%; D: 95.7%, L: 4.3%), 11.7 parts (0.2 mol) of magnesium hydroxide and 100 parts of water is dissolved by stirring for 20 minutes using a high-speed stirrer. After removing the water by distillation, 91 parts of D-CMPP-magnesium having an acid content of 91.7% are obtained, consisting of 95.7% D and 4.3% L enantiomer of m.p. >300° C., which corresponds to a yield of 99.3%.

The salts or salt mixtures prepared in these ways are completely water-soluble.

EXAMPLE 27

Potassium D-2-methyl-4-chlorophenoxypropionate 14 parts (0.14 mol) of potassium hydrogen carbonate are introduced into a melt of 21.4 parts (0.1 mol) of D-CMPP (D+L content 98.3%; D: 97.4% L: 2.6%) at 130° C., $CO_2$ being released. Residual amounts of water are removed in a water-jet vacuum. 28.8 parts of D-CMPP-potassium having an acid content of 72.0% are obtained, consisting of 97.4% D and 2.6% L enantiomer—of m.p. 190° C.–195° C., which corresponds to a yield of 95.3%.

We claim:

1. A process for preparing solid, free-flowing water-soluble salts of aryloxy-$C_1$–$C_4$-alkanecarboxylic acids, which comprises reacting the aryloxy-$C_1$–$C_4$-alkanecarboxylic acids with a salt-forming base, the salt formation taking place in the melt in the absence of an entraining agent and then isolating the solid salts.

2. A process as claimed in claim 1, wherein the salt-forming base used is a hydroxide, oxide, carbonate, acetate or formate of alkali metals or alkaline earth metals; ammonia or $C_1$–$C_4$-alkylamines.

3. A process as claimed in claim 1, wherein optically active 2-aryloxypropionic acids or their salts are used as starting materials and these are converted into the solid water-soluble salts with retention of the optical activity.

4. A process as claimed in claim 1, wherein a mixture of salts of various aryloxy-$C_1$–$C_4$-alkanecarboxylic acids is prepared.

5. A process as claimed in claim 4, wherein solid, free-flowing salts of the following mixtures are prepared:
dichlorprop-P and 2,4-D;
dichlorprop-P and MCPA;
mecoprop-P and 2,4-D;
mecoprop-P and MCPA;
MCPA and 2,4-D;
mecoprop-P, dichlorprop-P and MCPA.

6. A process as claimed in claim 1, wherein the salts of aryloxy-$C_1$–$C_4$-alkanecarboxylic acids are prepared in a mixture with the corresponding salts of other herbicides, selected from the group consisting of bentazone, glyphosate, glufosinate, ioxynil, bromoxynil and dicamba.

* * * * *